US006441178B2

(12) United States Patent
Zavareh et al.

(10) Patent No.: US 6,441,178 B2
(45) Date of Patent: Aug. 27, 2002

(54) RESOLUTION OF RITALINIC ACID SALT

(75) Inventors: Hooshang Shahriari Zavareh, Cambridge; Gerard Andrew Potter, Leicester, both of (GB)

(73) Assignee: Medeva Europe Limited (GB)

( * ) Notice: Subject to any disclaimer, the term of this patent is extended or adjusted under 35 U.S.C. 154(b) by 0 days.

(21) Appl. No.: 09/487,071

(22) Filed: Jan. 19, 2000

Related U.S. Application Data

(63) Continuation of application No. 09/008,152, filed on Jan. 16, 1998, now abandoned.
(60) Provisional application No. 60/041,254, filed on Mar. 17, 1997.

(30) Foreign Application Priority Data

Jan. 17, 1997 (GB) ............................................ 97000912

(51) Int. Cl.[7] ............................................ C07D 211/32
(52) U.S. Cl. ........................ 546/238; 546/237; 546/239
(58) Field of Search ................................. 546/237, 238, 546/239

(56) References Cited

U.S. PATENT DOCUMENTS

| 2,957,880 A | 10/1960 | Rometsch | 546/233 |
| 4,285,964 A | 8/1981 | Niebes et al. | 514/457 |
| 5,162,344 A | 11/1992 | Koch | 514/356 |

FOREIGN PATENT DOCUMENTS

| WO | 9728124 | 8/1997 |
| WO | 9732851 | 9/1997 |

OTHER PUBLICATIONS

Sakai et al. "Preparation of optically active alphs–methyl . . . " CA 120:299229 (1994).*
Patrick, K.S., Caldwell, R.W., Ferris, R.M., Breese, G.R. (1987) "Pharmacology of the enantioimers of threo–methylphenidate" *Chemical Abstracts* 107(3):17710, abstract number 17704h.

Corey, E.J., Mann, J. (1973) "A New Stereocontrolled Synthesis of Prostaglandins via Prostaglandin A2" *Journal of the American Chemical Society* 95(20):6832–6833.

Yakhontov, L.N., Levkoeva, E.I. (1975) "Methyl threo–α–(2–piperidyl) acetate hydrochloride" *Chemical Abstracts* 83(13):538.

Newman, P. (1981) "Optical Resolution Procedures for Chemical Compounds" (Riverdale, New York) vol. 2, Acids, Part I, p. 2.

Nohira, H. (1983) "Separation of enantiomers and racemates from partically optically–active mandelic acid" 3 pp. (abstract only 99:38206 CA).

Vincze, Irene et al. (1996) "Steroids 54. Amino acylamidosteroids" *Steroids* 61(12):697–702 (abstract only 126:104294 CA).

Vernin, Jean Marie "Antiasthenic compositions containing a double salt of ascorbic acid and amino diacids" 7 pp. (abstract only 100:91356 CA).

Societe d'Etudes et Applications Chimiques, Fr. "Soluble organic compounds containing sulfur" 11 pp. (abstract only 85:14144 CA).

Lugosi, Gyorgy et al. "Pyridinediols as feed additives" 4 pp. (abstract only 70:19044 CA).

Acta Exp. Chem. Japan (1958) *Chemical Society*, vol. 18, pp. 504–505.

* cited by examiner

*Primary Examiner*—Ceila Chang
(74) *Attorney, Agent, or Firm*—Saliwanchik Lloyd & Saliwanchik

(57) ABSTRACT

A process for preparing an enantiomerically-enriched form of threo-ritalinic acid, which comprises resolving a mixture of enantiomers of a salt of the acid, said salt being formed with an achiral acid or base, using a chiral resolving agent. The resolved salt can be esterified, to give the therapeutic agent d-threo-methylphenidate.

10 Claims, No Drawings

RESOLUTION OF RITALINIC ACID SALT

CROSS-REFERENCE TO RELATED APPLICATIONS

This application is a continuation of co-pending application U.S. Ser. No. 09/008,152, filed Jan. 16, 1998 now abandoned, which claims the benefit of provisional application U.S. Ser. No. 60/041,254, filed Mar. 17, 1997.

FIELD OF THE INVENTION

This invention relates to an economic process for the manufacture of a single isomer of a precursor to d-threo-methylphenidate.

BACKGROUND TO THE INVENTION

Methylphenidate is a therapeutic agent that is widely used in the treatment of attention-deficient hyperactivity disorder. It is a controlled substance.

Methylphenidate was first prepared as a mixture of the erythro [R*S*] and threo [R*R*] racemates. U.S. Pat. No. 2,957,880 discloses studies upon the two racemic mixtures, which revealed that the therapeutic activity resides in the threo diastereoisomer. It is now considered that it is the d-threo [or (R,R)] enantiomer that has the preferred therapeutic activity. Uses of this enantiomer are disclosed in WO-A-9703671, WO-A-9703672 and WO-A-9703673, the contents of which are incorporated herein by reference.

The resolution of threo methylphenidate can be achieved using the expensive resolving agent 1,1'-binaphthyl-2,2'-diyl hydrogen phosphate, a process first reported by Patrick et al, The Journal of Pharmacology and Experimental Therapeutics, 241:152–158 (1987). More efficient resolutions, using a O,O'-diaroyltartaric acid or menthoxyacetic acid, are disclosed in WO-A-9727176 and in PCT/GB97/00643, the contents of which are incorporated by reference; in particular, the use of O,O'-di-p-toluoyltartaric acid allows the diastereoisomeric salts to be very readily separated, to give the desired enantiomer in high enantiomeric excess and high chemical purity.

In an alternative approach, disclosed in U.S. Pat. No. 2,957,880, the amide of erythro methylphenidate (i.e. as —$CONH_2$ instead of —$CO_2Me$) is resolved using tartaric acid. However, this resolution must be followed by amide hydrolysis, and equilibration at the benzylic center, to give the threo isomer of the carboxylic acid which is esterified.

It would be desirable to find a satisfactory substrate for resolution that did not involve handling the active drug. Ritalinic acid might be a target, and is a common intermediate, in threo form, in synthesis preceding or following the two respective resolutions described above.

U.S. Pat. No. 2,957,880 discloses single isomer ritalinic acid hydrochloride. It is prepared (see Example 6) from the corresponding acid amide.

SUMMARY OF THE INVENTION

The present invention is based on the surprising discovery that, although ritalinic acid will not undergo any effective degree of resolution with any of a wide range of resolving agents, a salt thereof is an effective substrate for resolution, e.g. with a chiral base. In a particular preferred embodiment of the invention, threo-ritalinic acid hydrochloride is resolved with (−)-1-phenylethyl amine. The chiral base may form a novel double salt.

DESCRIPTION OF THE INVENTION

For the purposes of illustration at least, the salt that is the substrate for resolution according to this invention may be prepared by base hydrolysis of methylphenidate, using NaOH or another hydroxide (MOH). A suitable acid salt may then be prepared by adding an acid (HX) that releases M from the resultant salt (e.g. a metal or ammonium salt) of ritalinic acid. On passing the isoelectric point, it appears that the piperidine N atom is protonated. Alternatively, preparation of salts may be via acid hydrolysis of methylphenidate.

The resolution is conducted using conditions that are generally known in the art. Examples of suitable chiral bases are 1-phenylethylamine, and also 1-(1-naphthyl) ethylamine, cinchonine, cinchonidine and N-methyl-D-glucamine. The use of, say, (−)-1-phenylethylamine gives the preferred d-threo-enantiomer of ritalinic acid salt. That can be converted to d-threo-methylphenidate hydrochloride by reaction with methanol and HCl, with heating.

Salts that are substrates for resolution according to this invention have good or at least adequate solubility in various solvents, especially polar solvents, including aqueous systems. Adjustment of pH, e.g. by adding acid (which may be ritalinic acid), can enhance solubility.

The following Example illustrates the invention.

EXAMPLE

A solution of dl-threo-methylphenidate (1 g) in water (25 ml) and conc. HCl (5 ml) was heated under reflux for 3 h. The clear solution was evaporated to dryness, to give a dl-threo-ritalinic acid hydrochloride as a white solid.

Resolution was performed using this salt. The salt (175 mg; 0.8 mmol) was placed in a 10 ml round-bottom flask. Ethanol (5 ml) was added, to give a clear solution. (−)-1-Phenylethylamine (0.1 ml; 0.8 mmol) was added. A gelatinous precipitate formed after a few minutes. Water (15 drops) was added, and the mixture stirred for 2 h. White crystals formed within 1 h. Following stirring overnight, crystals (40 mg) were collected on a sinter. Chiral HPLC analysis showed the crystals to comprise a diastereoisomeric salt enriched in d-threo-ritalinic acid, of 77% ee, and the mother liquors containing the opposite diastereoisomer enriched in l-threo-ritalinic acid, of at least 23% ee.

A crystalline ritalinate salt is formed when ritalinic acid hydrochloride is mixed with 1-phenylethylamine but does not form when the ritalinic free amino-acid is mixed with 1-phenylethylamine. NMR shows that this salt contains ritalinate and is thus not simply 1-phenylethylamine hydrochloride. From these observations, it is deduced that the salt is the double salt depicted below. The salt is also a hydrate, since only a gelatinous precipitate is formed in anhydrous ethanol, whereas in 95% ethanol/5% water white crystals are formed.

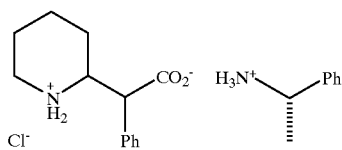

We claim:

1. A process for preparing an enantiomerically-enriched form of a double salt of threo-ritalinic acid having two counterions, wherein said double salt has a 1:2 ratio of acid:counterion, comprising forming a threo-ritalinic acid addition salt using an achiral acid and then resolving enantiomers of said achiral acid addition salt with a single chiral resolving base.

2. The process according to claim 1, wherein said acid addition salt is the hydrochloride.

3. The process according to claim 1, wherein the enantiomeric enrichment is at least 70%.

4. The process according to claim 1, wherein said resolving base is a chiral amine.

5. The process according to claim 4, wherein said amine is (-)-1-phenylethylamine.

6. The process according to claim 1, wherein the d-enantiomer of threo-ritalinic acid is enantiomerically-enriched.

7. A process for preparing d-threo-methylphenidate, which comprises conducting a process according to claim 6 and then subjecting the product to reaction with methanol or esterification with a methylating agent.

8. A double salt of threo-ritalinic acid, predominantly as a single enantiomer thereof, comprising one anionic counterion and one cationic counterion, wherein said anionic counterion is achiral and the other is derived from a single enantiomer chiral resolving agent.

9. The double salt according to claim 8, wherein the chiral counterion is an amine.

10. The double salt according to claim 8, wherein the chiral counterion is (-)-1-phenylethylamine.

* * * * *